US009308367B2

(12) United States Patent  
Chambers et al.

(10) Patent No.: US 9,308,367 B2  
(45) Date of Patent: Apr. 12, 2016

(54) SENSITIVE MEASUREMENTS IN A HEARING PROSTHESIS

(71) Applicant: Cochlear Limited, Macquarie University, NSW (AU)

(72) Inventors: John Chambers, Mona Vale (AU); Mathew Ross Markey, Oatley (AU); David John Reid, Forestville (AU); Padraig Hurley, Frenchs Forest (AU)

(73) Assignee: Cochlear Limited, Macquarie University, NSW ( * ) Notice: Subject to any disclaimer, the term of this patent is extended or adjusted under 35 U.S.C. 154(b) by 0 days.

(21) Appl. No.: 14/579,104

(22) Filed: Dec. 22, 2014

(65) Prior Publication Data

US 2015/0105841 A1  Apr. 16, 2015

Related U.S. Application Data

(62) Division of application No. 13/040,815, filed on Mar. 4, 2011, now abandoned.

(51) Int. Cl.
*A61N 1/36* (2006.01)
*A61N 1/378* (2006.01)
*A61N 1/05* (2006.01)

(52) U.S. Cl.
CPC .......... *A61N 1/36032* (2013.01); *A61N 1/3782* (2013.01); *A61N 1/0541* (2013.01)

(58) Field of Classification Search
CPC . A61N 1/0541; A61N 1/36032; A61N 1/365; A61N 1/3702; A61B 5/0484
See application file for complete search history.

(56) References Cited

U.S. PATENT DOCUMENTS

| 5,876,425 | A | 3/1999 | Gord et al. |
| 6,208,896 | B1 * | 3/2001 | Mulhauser ........................ 607/5 |
| 6,415,186 | B1 | 7/2002 | Chim et al. |
| 2004/0247148 | A1 * | 12/2004 | Pedersen ....................... 381/323 |
| 2006/0031736 | A1 * | 2/2006 | Fahlenkamp et al. ......... 714/755 |
| 2006/0235490 | A1 * | 10/2006 | Killian ............... A61N 1/36032 607/60 |
| 2006/0271110 | A1 | 11/2006 | Vernon et al. |
| 2007/0179565 | A1 * | 8/2007 | Overstreet et al. .............. 607/57 |

OTHER PUBLICATIONS

Examination Report in counterpart European Application No. 12755285.9, mailed Sep. 17, 2014, 6 pages.

* cited by examiner

*Primary Examiner* — Theodore Stigell
*Assistant Examiner* — Natasha Patel

(57) ABSTRACT

Aspects of the present invention are generally directed to taking measurements in a hearing prosthesis. In an embodiment, a power circuit, which may be a switched mode power circuit, is shut down during performance of the measurements to reduce interference. Then, power capacitively stored by the power circuit is used to power the hearing prosthesis during performance of the measurements. In an embodiment, the power circuit increases its voltage just prior to performance of the measurements. This serves to increase the amount of energy capacitively stored by the power circuit and thus extends the period of time during which the measurements may be taken while the power circuit is shut off.

20 Claims, 8 Drawing Sheets

SENSITIVE MEASUREMENTS IN A HEARING PROSTHESIS

CROSS-REFERENCE TO RELATED APPLICATIONS

This application is a divisional of U.S. patent application Ser. No. 13/040,815, entitled "Sensitive Measurements In A Hear Prosthesis", filed Mar. 4, 2011, which are hereby incorporated by reference herein.

BACKGROUND

1. Field of the Invention

The present invention relates generally to hearing prostheses, and more particularly, to measurements in a hearing prosthesis.

2. Related Art

Hearing loss, which may be due to many different causes, is generally of two types, conductive or sensorineural. In many people who are profoundly deaf, the reason for their deafness is sensorineural hearing loss. This type of hearing loss is due to the absence, destruction or damage to the hairs in the cochlea which transduce acoustic signals into nerve impulses. Various hearing prostheses have been developed to provide individuals suffering from sensorineural hearing loss with the ability to perceive sound.

One type of hearing prosthesis, referred to as a cochlear implant system, includes an electrode assembly implanted in the cochlea. Electrical stimulation signals are delivered directly to the auditory nerve via the electrode assembly, thereby inducing a hearing sensation in the implant recipient.

Conductive hearing loss occurs when the normal mechanical pathways which conduct sound to the cochlea are impeded. This problem may arise, for example, as a result of damage to the ossicular chain or ear canal. Individuals suffering from conductive hearing loss frequently retain some form of residual hearing because the hairs in the cochlea are often undamaged. For this reason, individuals who suffer from conductive hearing loss typically are not candidates for a conventional cochlear implant system because insertion of the electrode assembly into the cochlea may severely damage or destroy the remaining hairs in the cochlea.

Individuals suffering from conductive hearing loss typically receive an acoustic hearing aid. Hearing aids receive ambient sound, amplify the sound, and direct the amplified sound through the ear canal. The amplified sound reaches the cochlea and causes motion of the cochlea fluid, thereby stimulating the hairs in the cochlea.

Unfortunately, hearing aids do not benefit all individuals suffering from conductive hearing loss. For example, some individuals are prone to chronic inflammation or infection of the ear canal. Other individuals have malformed or absent outer ear and/or ear canals as a result of a birth defect, or as a result of common medical conditions such as Treacher Collins syndrome or Microtia.

Individuals unable to benefit from hearing aids may benefit from implantable hearing prostheses that deliver mechanical energy to the recipient. In one type of implantable hearing prosthesis, an implanted actuator is rigidly connected to the ossicular chain, thereby enabling direct vibration of the ossicular chain to induce an auditory response. In another type of hearing prosthesis, an implanted actuator is rigidly connected to the cochlea and operates by directly vibrating the perilymph in the inner ear. Both of these types of hearing prostheses often require complicated surgery, and they are not well-suited for implantation into growing children because of the rigid connections between the actuator and the ossicular chain and perilymph, respectively.

Another type of hearing prosthesis, referred to as a bone conduction device, such as a Baha®, has an actuator implanted into the skull bone of the recipient. The actuator provides vibrations directly to the recipient's skull bone. These vibrations are conducted by the recipient's bony structure to the inner ear to elicit an auditory response.

SUMMARY

In one aspect of the invention, there is a method for performing an evoked compound action potential (ECAP) measurement using a cochlear implant system having a switch mode voltage conversion circuit that interferes with the ECAP measurement while it is performed. The method comprises increasing a voltage supplied by the switch mode voltage conversion circuit until sufficient energy is stored in an energy storage device connected to the switch mode voltage conversion circuit; shutting down the switch mode voltage conversion circuit; and performing the ECAP measurement using the cochlear implant system, wherein the ECAP measurement is performed while the switch mode voltage conversion circuit is shut down.

In another aspect, there is a method for performing an evoked compound action potential (ECAP) measurement using a cochlear implant system having a stimulator unit and having interfering circuits within the stimulator unit that interfere with the ECAP measurement while it is performed. The method comprises terminating power to the interfering circuits; and performing the ECAP measurement using the cochlear implant system while the power to the interfering circuits is terminated.

In yet another aspect, there is provided a cochlear implant system. The cochlear implant system comprise a stimulation circuit configured to apply stimulation to cause a hearing percept by a recipient; a power circuit configured to provide power to the stimulation circuit; a switch mode voltage conversion circuit connected to an energy storage device; a measurement control circuit configured to perform an evoked compound action potential (ECAP) measurement using the cochlear implant system; and a measurement sequence controller configured to instruct the switch mode voltage conversion circuit to increase a voltage it supplies prior to the ECAP measurement being performed until sufficient energy is stored in the energy storage device, and wherein the measurement sequence controller is configured to shut down the switch mode voltage conversion circuit during performance of the ECAP measurement

BRIEF DESCRIPTION OF THE DRAWINGS

Illustrative embodiments of the present invention are described herein with reference to the accompanying drawings, in which.

DETAILED DESCRIPTION

Embodiments of the present invention are generally directed to taking measurements in a hearing prosthesis. In an embodiment, the power circuit, which may be a switched mode power circuit, is shut down during performance of the measurements to reduce interference. Then, power capacitively stored by the power circuit is used to power the hearing prosthesis during performance of the measurements. In an embodiment, the power circuit increases its voltage just prior to performance of the measurements. This serves to increase the amount of energy capacitively stored by the power circuit and thus extends the period of time during which the measurements may be taken while the power circuit is shut off.

Embodiments of the present invention are described herein primarily in connection with one type of hearing prosthesis, namely a cochlear prostheses (commonly referred to as cochlear prosthetic devices, cochlear implant systems, cochlear implants, cochlear devices, and the like; simply "cochlea implant systems" herein.) Cochlear implant systems generally refer to hearing prostheses that deliver electrical stimulation to the cochlea of a recipient. As used herein, cochlear implant systems also include hearing prostheses that deliver electrical stimulation in combination with other types of stimulation, such as acoustic or mechanical stimulation. It would be appreciated that embodiments of the present invention may be implemented in any cochlear implant system or other hearing prosthesis now known or later developed, including auditory brain stimulators, or implantable hearing prostheses that acoustically and/or mechanically stimulate components of the recipient's middle or inner ear.

Figure 1:
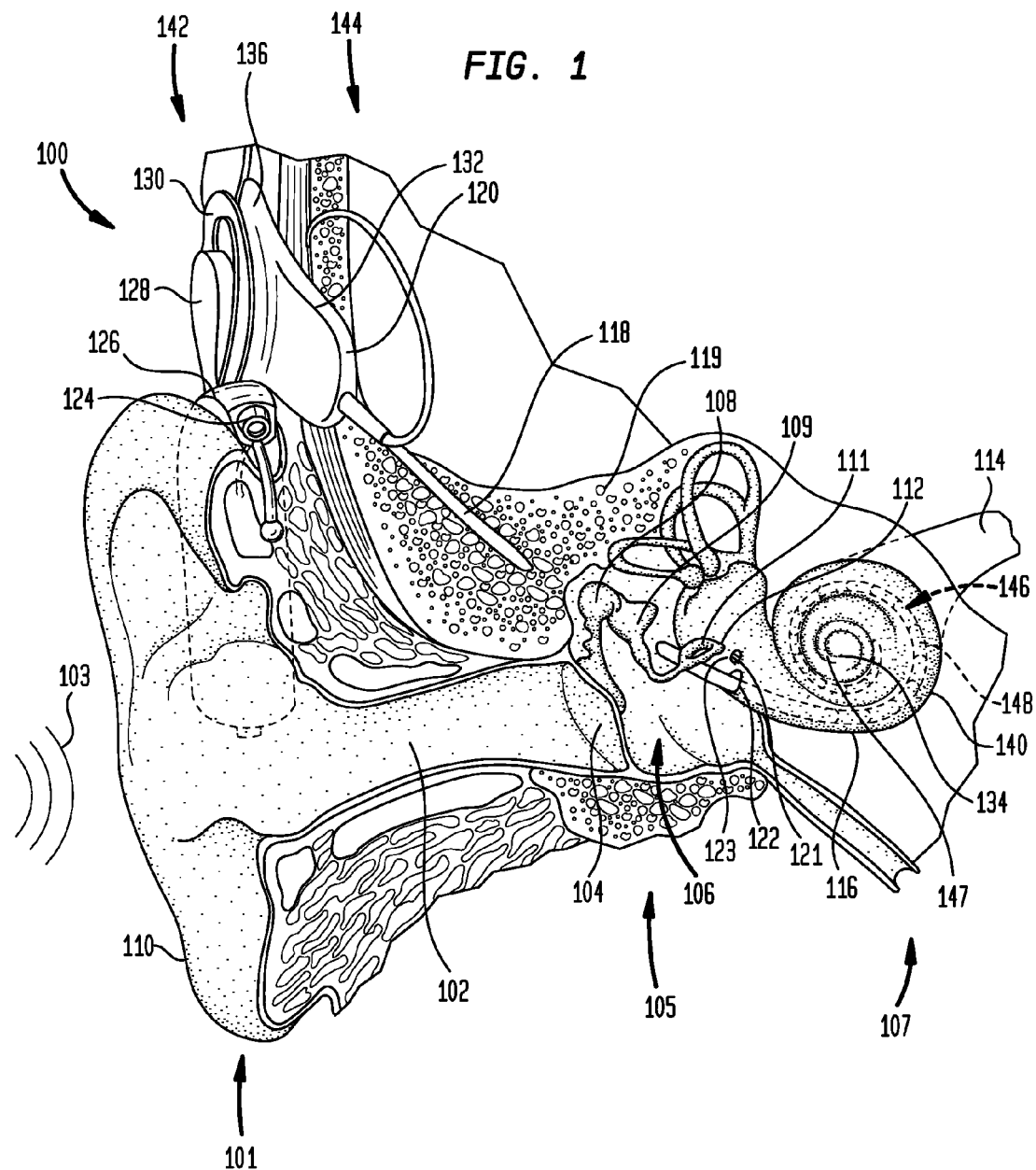
FIG. 1 is a perspective view of a cochlear implant system in which embodiments of the present invention may be implemented.
Figure 2:
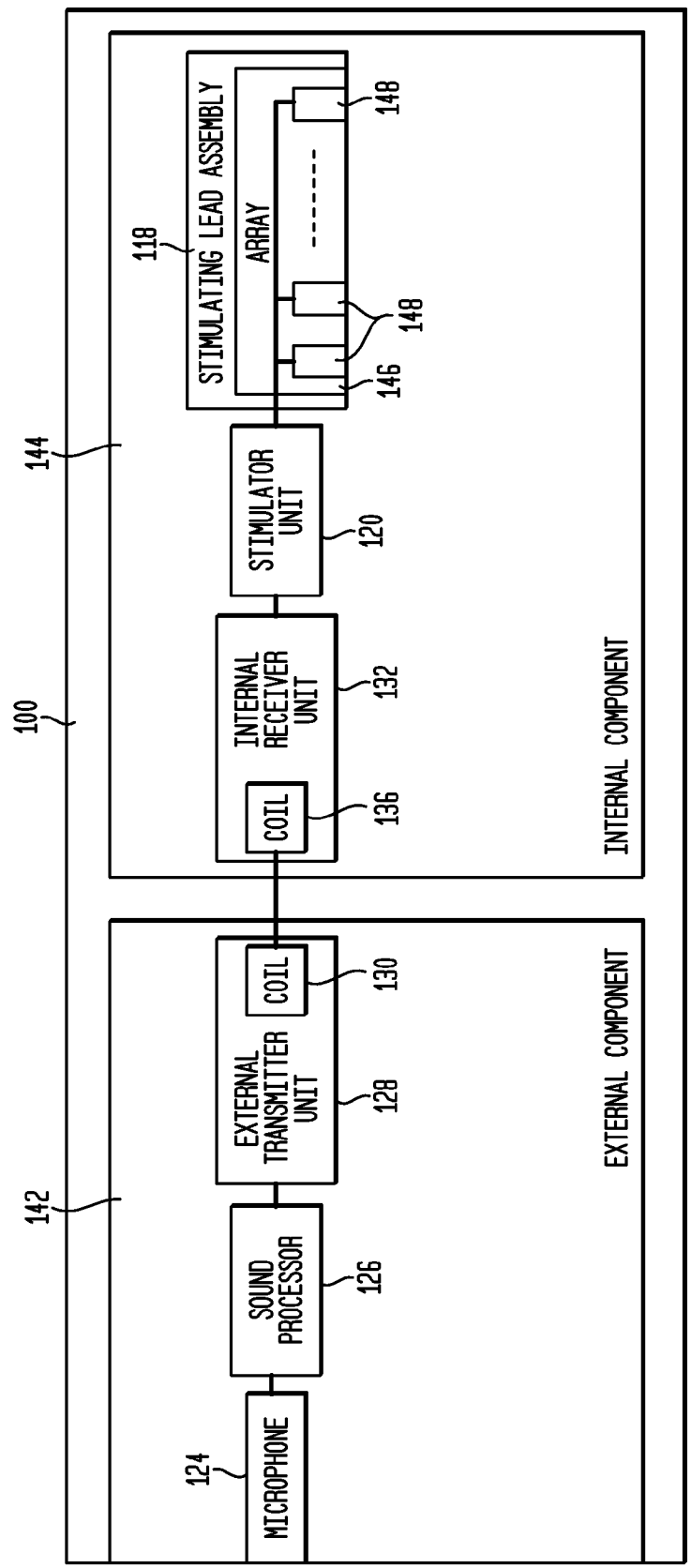
FIG. 2 is a functional block diagram of the cochlear implant system of FIG. 1, in accordance with an embodiment of the present invention.

FIG. 1 is perspective view of a cochlear implant system, referred to as cochlear implant system 100 implanted in a recipient. FIG. 2 is a functional block diagram of cochlear implant system 100. The recipient has an outer ear 101, a middle ear 105 and an inner ear 107. Components of outer ear 101, middle ear 105 and inner ear 107 are described below, followed by a description of cochlear implant system 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant system 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processor 126, a power circuit (not shown), and an external transmitter unit 128. External transmitter unit 128 comprises an external coil 130 and, preferably, a magnet (not shown) secured directly or indirectly to external coil 130. Sound processor 126 processes the output of microphone 124 that is positioned, in the depicted embodiment, by auricle 110 of the recipient. Sound processor 126 generates encoded signals, sometimes referred to herein as encoded data signals, which are provided to external transmitter unit 128 via a cable (not shown). Sound processor 126 may further comprise a data input interface (not shown) that may be used to connect sound processor 126 to a data source, such as a personal computer or musical instrument (e.g., a MIDI instrument).

Internal component 144 comprises an internal receiver unit 132, a stimulator unit 120, and a stimulating lead assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130. Stimulating lead assembly 118 has a proximal end connected to stimulator unit 120, and a distal end implanted in cochlea 140. Stimulating lead assembly 118 extends from stimulator unit 120 to cochlea 140 through mastoid bone 119. In some embodiments stimulating lead assembly 118 may be implanted at least in basal region 116, and sometimes further. For example, stimulating lead assembly 118 may extend towards apical end of cochlea 140, referred to as cochlea apex 134. In certain circumstances, stimulating lead assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating lead assembly 118 comprises a longitudinally aligned and distally extending array 146 of electrode contacts 148, sometimes referred to as array of electrode contacts 146 herein. Although array of electrode contacts 146 may be disposed on stimulating lead assembly 118, in most practical applications, array of electrode contacts 146 is integrated into stimulating lead assembly 118. As such, array of electrode contacts 146 is referred to herein as being disposed in stimulating lead assembly 118. Stimulator unit 120 generates stimulation signals which are applied by electrode contacts 148 to cochlea 140, thereby stimulating auditory nerve 114. Because, in cochlear implant system 100, stimulating lead assembly 118 provides stimulation, stimulating lead assembly 118 is sometimes referred to as a stimulating lead assembly.

In cochlear implant system 100, external coil 130 transmits electrical signals (that is, power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

As noted above, in an embodiment, cochlear implant system 100 may be configured for making sensitive measurements in addition to applying stimulation for invoking a hearing perception. These sensitive measurements may include evoked compound action potential (ECAP) measurements, such as neural response telemetry (NRT) measurements. A neural response telemetry device is a computerized system that allows for measurement of the ECAP response of the auditory nerve evoked by electrical stimulation applied by electrodes implanted in the cochlea. As such, neural response telemetry allows a clinician to set parameters for the cochlear implant system 100 that do not rely on subjective observations. Such a system is in clinical use by practitioners for adjustment of prosthetic hearing implants.

An advantage of neural response telemetry is that it does not require the recipient to pay attention or remain immobile, which notably allows for use with infants. One exemplary computerized system that uses neural response telemetry is the Nucleus® NRT™ 3.0, commercially available from Cochlear Limited, Australia. In an embodiment, the ECAP measurements may involve measuring millivolt signals that appear across electrodes. Further, these measurements may involve taking a number of ECAP measurements, each on the order of milliseconds, over a period of one or more seconds to, for example, average out noise.

Although the present embodiment will be discussed with reference to a cochlear implant system configured to take ECAP measurements, it should be noted that in other embodiments other devices and types of measurements may be used, such as sound, mechanical vibration, light, body temperature, chemical changes, electrical impedance, voltage, current, and electromagnetic field measurements.

The small internal volume of hearing prostheses, such as a cochlear implant system intended for implantation within the head of an adult, child, or infant, severely limit the degree by which sensitive measurement circuitry can be physically or electrically separated or shielded from internal sources of electrical interference. As a consequence, electrical, magnetic, or electromagnetic energy radiated from adjacent circuitry has the potential to overwhelm or add unwanted signal artifacts to the measurements. This has the potential to degrade the accuracy of the measurements, the safety of the prosthesis, and/or the benefit it delivers to the user.

In a cochlear implant system, such as cochlear implant system 100, potential sources of interference may include circuitry associated with wireless communications (e.g., communications between external transmitter unit 128 and internal transmitter unit 132), power control and switch mode power supplies, digital event sequencing, information processing, and neural stimulation delivery (i.e., the application of stimulation to evoke a hearing percept).

An embodiment of the present invention, includes circuitry configured to eliminate or reduce this interference and thus improve the accuracy of the sensitive measurements. As will be discussed further below, this circuitry may be configured to disable or modify the operation of potentially interfering electrical circuits during periods when sensitive measurements are undertaken. This may be accomplished in a strategic manner to both minimize the interference while minimizing the impact that these adjustments have on the overall operation of the hearing prosthesis.

Figure 3:
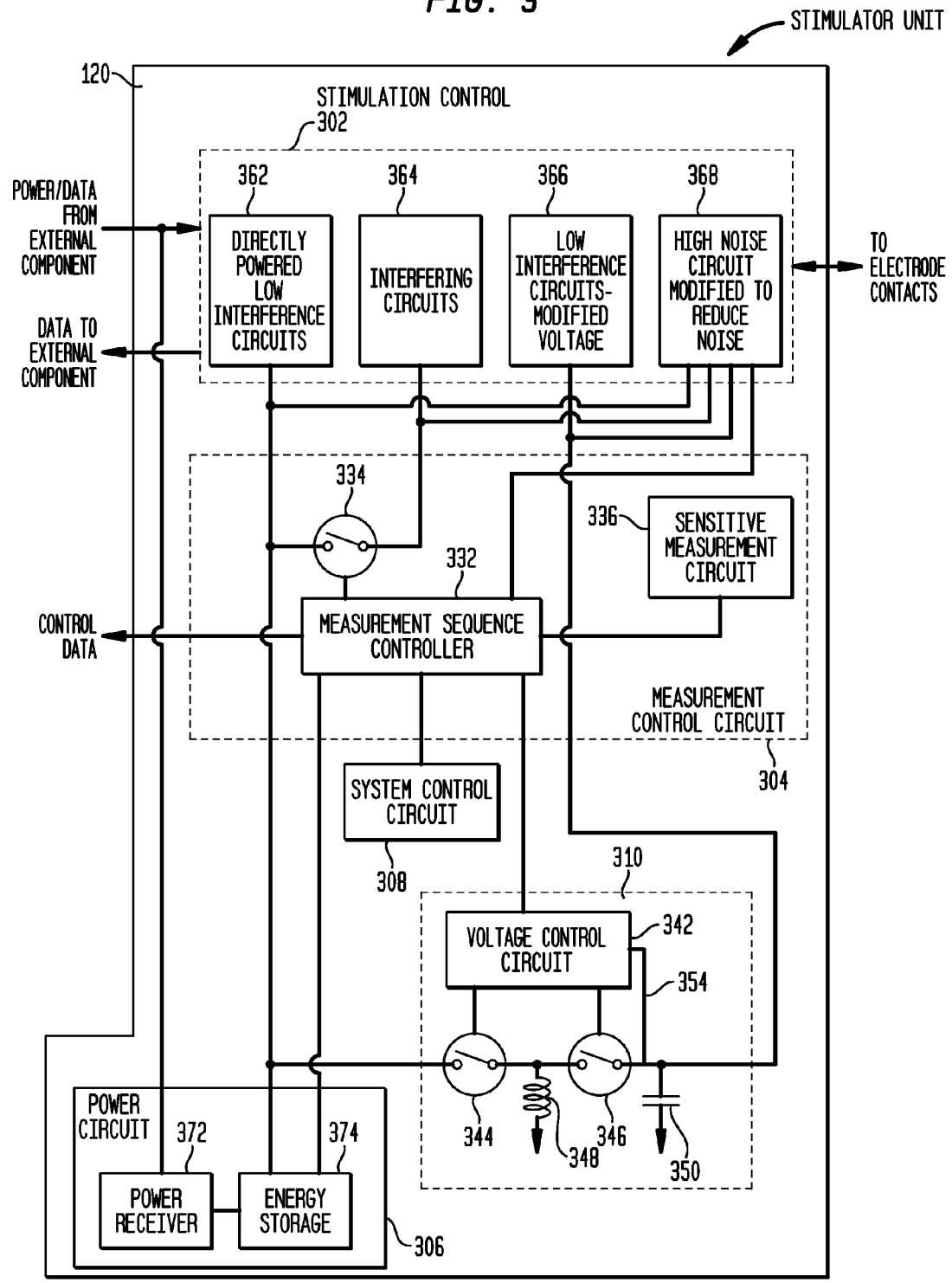
FIG. 3 is a block diagram of a stimulator unit 120, in accordance with an embodiment of the present invention.

FIG. 3 is a block diagram of an embodiment of stimulator unit 120, referred to here as stimulator unit 320. As illustrated, stimulator unit 120 comprises a stimulation circuit 302, a measurement control circuit 304, a power circuit 306, and a system control circuit 308. System control circuit 308 may be a circuit configured to exercise control over the other components of stimulator unit 320. Stimulation circuit 302 comprises the circuitry for receiving the encoded data signals from the external component 142 (FIG. 1), generating stimulation signals corresponding to the encoded data signals, and sending the stimulation signals to the electrode contacts 148 (FIG. 1) for application of stimulation to the recipient. Stimulation circuit 302 may further comprise circuitry for receiving signals from the electrode contacts 148 (FIG. 1), generating telemetry data from the signals, and sending the telemetry data to the external component 142 (FIG. 1).

Power circuit 306 comprises circuitry for powering the internal component 144 (FIG. 1) and as illustrated may include a power receiver 372 and an energy storage component 374. Power receiver 372 may comprise circuitry for separating out the power component from the power/data signal received from the external component 142 (FIG. 1). Energy storage component 374 may comprise one or more capacitors and/or one or more batteries for storing power for use by stimulator unit 120. For example, energy storage component 374 may comprise a rechargeable battery configured to store power received from the external component 142 (FIG. 1). This may permit the recipient to use a larger external component at certain times (e.g., at night) to recharge power circuit 306, and then during other times (e.g., during periods that the recipient is active) use a smaller external component that provide data, but not power, to the internal component.

In an embodiment, power circuit 306 may be a configured to provide sufficient voltage for the application of stimulation (i.e., the stimulation signals) to induce a hearing percept in the recipient. As used herein, the term power circuit refers to any type of circuit configured to output a signal that may be used to provide power for one or more other circuits (e.g., a circuit comprising one or more components). For example, exemplary power circuits may comprise one or more of a battery, a capacitor, a switch mode voltage conversion circuit, etc.

As illustrated, power circuit 306 is directly connected to certain circuits 362, referred to as directly powered low interference circuits 362. These circuit 362 may include, for example, analog to digital converter(s) (ADCs) (or parts thereof) for capturing the sensitive measurement, bias generators, band-gap references, critical linear power generators.

Power circuit 306 is also connected to certain interfering circuits 364 via a switch 334 that when open disconnects interfering circuits 364 from power circuit 306. Switch 334 thus enables interfering circuits 364 to be switched off during measurements. Exemplary interfering circuits may include, communication circuits, such as, RF, magnetic, transcutaneous or otherwise, signal processors and microprocessors. Further, in an embodiment, the power receiver 372 of power circuit 306 may be included in interfering circuits 364, such that power receiver 372 may be switched off during measurements.

Stimulator unit 120 also comprises a switch mode voltage conversion circuit 310, also sometimes referred to as a switch mode power circuit, switch mode power supply, etc. In embodiments, switch mode voltage conversion circuit 310 may be configured to generate repetitive, fast changing voltage and current transients in the application of stimulation to the recipient. In the absence of circuitry, such as disclosed herein, these transients may be such that they can overwhelm low amplitude neural response measurements as well as other signals from the recipient. Further, in an example, switch mode voltage conversion circuit 310 may be configured to convert the voltage from power circuit 306 to a different voltage. For example, power circuit 306 may provide a baseline output voltage of 5 volts during normal operations. Switch mode voltage conversion circuit 310 may be configured to covert the 5 volt signal from power circuit 306 to, for example, a 10 volt signal that may be used, for example, for providing stimulation to the recipient. Or, for example, in an embodiment, switch mode power circuit 310 may be used to convert the voltage signal to a 3 volt signal to power integrated circuits or other digital circuitry within stimulator unit 120. It should be noted that these numbers are arbitrary and the specifics of the operation of the switch mode voltage conversion circuit 310 may vary based on, for example, the intended use of the power signal output by the switch mode voltage conversion circuit 310.

As illustrated, switch mode voltage conversion circuit 310 comprises a voltage control circuit 342, two switches 344 and 346, an inductor 348, and a capacitor 350. Voltage control circuit 342 controls operations of circuit 310 and may adjust the voltage supplied by circuit 310 by strategically opening and closing switches 344 and 346 and monitoring the output voltage via feedback loop 354. It should be noted that this is a simplified figure for explanatory purposes and that other configurations may be used for implementing switch mode voltage conversion circuit 310.

As illustrated, switch mode voltage conversion circuit 310 outputs a voltage signal to certain low interference circuits 366. These low interference circuits 366 may include, for example, low interference circuits requiring continuous power at a voltage different to that of the power circuit 306 and include, for example, an electrode bias circuit, and electrode safety monitoring circuitry.

Also illustrated in stimulation circuit 302 are high noise circuits 368 that have their operation modified to lower noise during measurements (one "modification" may be to switch off such circuits). These circuits may include, for example, a neural stimulating circuit, charge pumps or switch-mode power supplies, clocks and/or oscillators. Because the individual circuits included in high noise circuits 368 may have different power supply requirements, they are illustrated as receiving power directly from power circuit 306, from power circuit 306 via switch 334, and from switch mode voltage power circuit 310. These circuits may also include one or more of the exemplary circuits discussed above with reference to interfering circuits 364 depending on the system implementation, the voltages required by the circuits, and/or the voltages generated by the switch-mode supply.

As noted above, stimulator unit 120 may receive a signal from the external component 142 (FIG. 1) comprising both power and data. Stimulation circuit 302 may separate the data from the received signal and use the received data for generating stimulation signals, such as discussed above.

Measurement control circuit 304 is configured to temporarily disable or modify the operation of the interfering components of stimulator unit 120 so as to reduce interference while sensitive measurements are undertaken. This may comprise modifying the behavior of the switch mode voltage conversion circuit 310 and other circuits (e.g., power circuit 306) to extend the period (e.g., by a second or more or by only milliseconds depending on the specific implementation) these and other potentially interfering circuits can be shut down or modified (e.g., their clock speed reduced) to reduce interference.

As illustrated, measurement control circuit 304 may comprise a measurement sequence controller 332, a switch 334, and a sensitive measurement circuit 336. Measurement sequence controller 332 comprises the circuitry for controlling the adjustments to the system (e.g., disabling or modifying the operation of circuits) during the measurement(s). In addition to modifying circuits included in the stimulator unit 120, in an embodiment, the measurement sequence controller 332 may also send instructions to other devices (e.g., an external component, another internal component) directing the external component to adjust its behavior. For example, in a cochlear implant system embodiment, measurement sequence controller 332 may send a command to an external component, such as the speech processor or external transmitter unit, directing the external component to not transmit power and/or data to the internal component during performance of the measurement. Or, for example, in embodiments, measurement sequence controller 332 may direct other devices, such as an implant programming system, a diagnostic system, or a charging system to modify its performance during performance of the measurement.

Sensitive measurement circuit 336 comprises the circuitry for performing the measurements, such as directing the application of stimulation and measuring signals responsive to the applied stimulation, such as in ECAP measurements.

Figure 4:
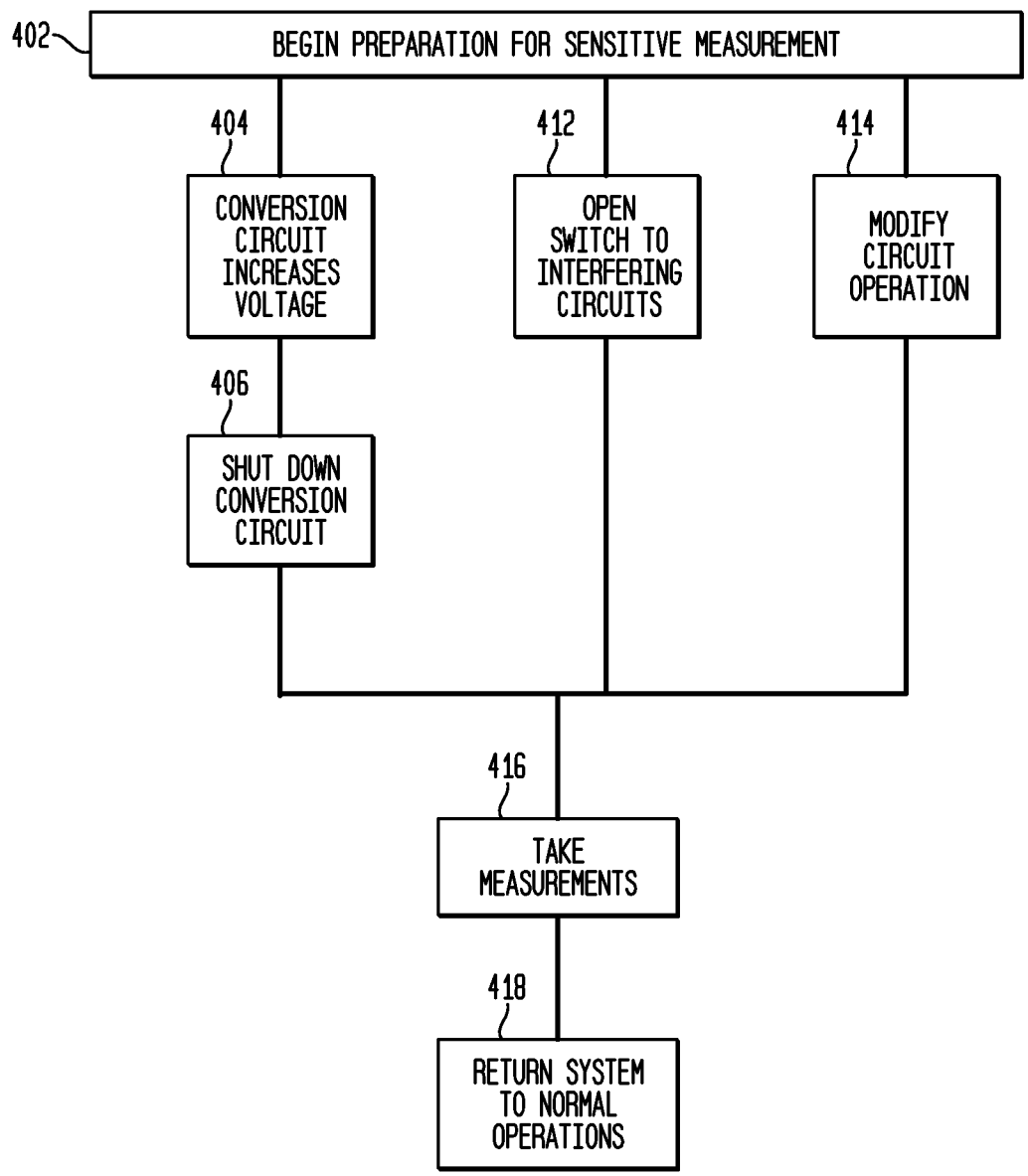
FIG. 4 is a flow chart of an exemplary method for reducing interference during sensitive measurements, in accordance with an embodiment of the present invention.

FIG. 4 is a flow chart of an exemplary method for reducing interference during sensitive measurements. FIG. 4 will be discussed with reference to stimulator unit 120 of FIG. 3 to help explain the operations of the components of measurement control circuit 304.

In operation, system control circuit 308 determines that a sensitive measurement is to be undertaken (e.g., an ECAP measurement) and instructs measurement sequence controller 332 to begin the process of preparing for the sensitive measurement at block 402. Measurement sequence controller 332 then, at block 404, instructs switch mode voltage conversion circuit 310 to momentarily increase the voltage it supplies to other circuits to a value above its normal operating value. After which, at block 406, the measurement circuit 304 may direct the switch mode voltage conversion circuit 310 to shut down or reduce its interfering behavior for a period of time during which the sensitive measurements are undertaken. For example, in an embodiment, measurement sequence controller 332 may direct, at block 404, voltage control circuit 342 to adjust the amount of time switches 344 and 346 are open and closed to cause the voltage stored by capacitor 350 to increase. After boosting the voltage stored by capacitor 350, measurement sequence controller 332 may, at block 406, open switches 344 and 346 to minimize the amount of interference generated by switch mode voltage circuit 310.

Figure 5:
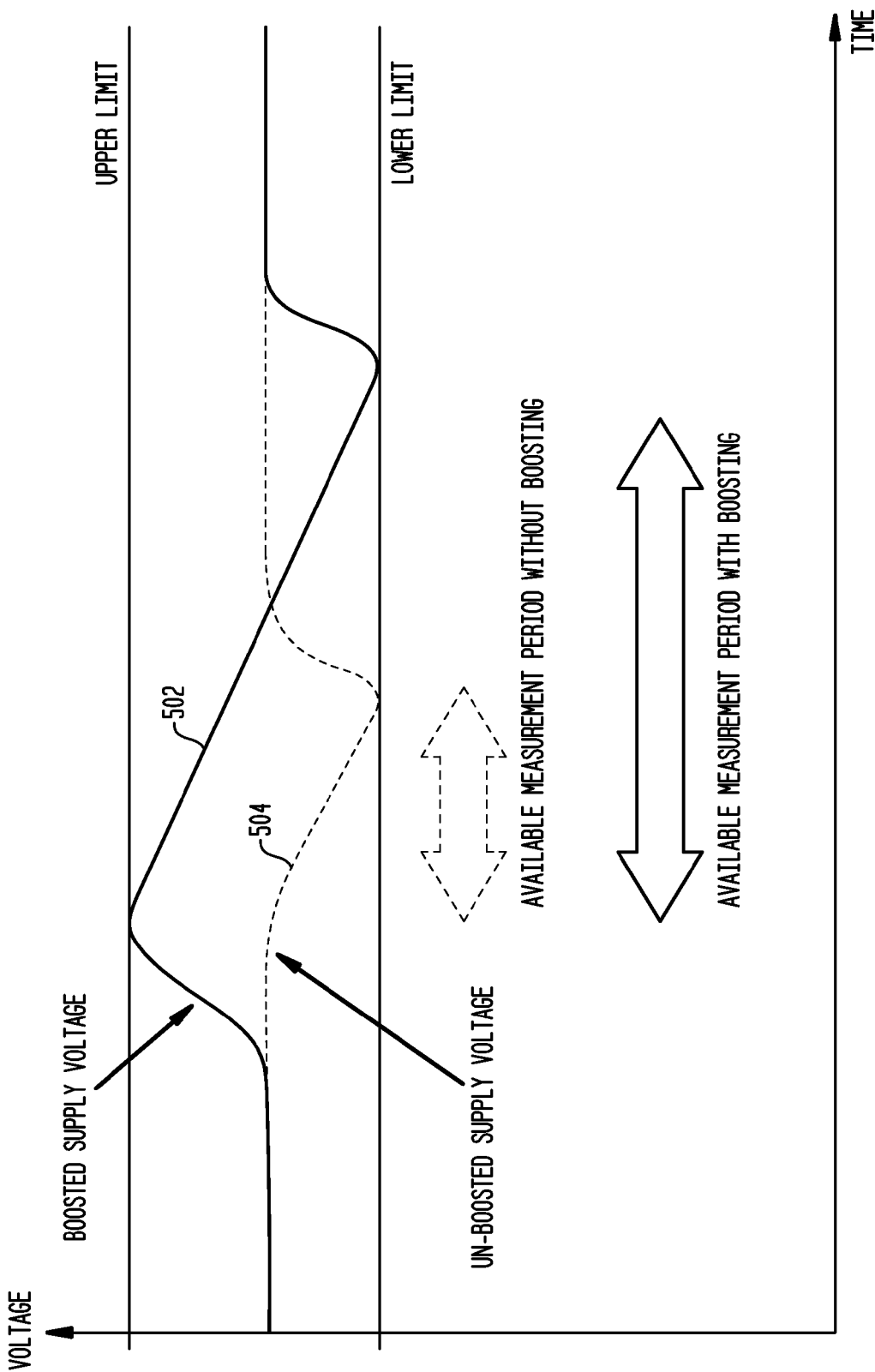
FIG. 5 illustrates a simplified exemplary voltage signal from a switch mode power circuit, in accordance with an embodiment of the present invention.

FIG. 5 illustrates a simplified exemplary voltage signal from a switch mode voltage conversion circuit, in accordance with an embodiment. Switch mode voltage conversion circuits normally exhibit a repetitive switching mode of operation during application of stimulation to the recipient. As illustrated, the voltage 502 of switch mode voltage conversion circuit 310 is initially at a base line value (e.g., 10 volts). Just prior to commencement of the measurements, the voltage 502 output by switch mode voltage conversion circuit 310 is increased (e.g., to a voltage of 15 volts). This voltage increase can help prolong the period of time during which the stimulator unit's 320 circuitry can operate on the available energy stored in capacitor 350 of switch mode voltage conversion circuit 310.

After increasing the voltage, the normally repetitive switching mode of the switch mode voltage conversion circuit 310 is disabled or modified and the sensitive measurements are initiated. During this period of time, energy stored in the capacitor 350 of switch mode voltage conversion circuit 310 is used to power the stimulator unit 120. This results in the voltage output from the switch mode voltage conversion circuit 310 decaying. For example, as illustrated, the voltage output from the switch mode voltage conversion circuit 310 may fall to a voltage of 5 volts. This lower limit (e.g., 5 volts) is the minimum amount of voltage for which the cochlear implant system 100 may operate, below which the circuits may not correctly function. As such, once this lower limit is reached, the hearing prosthesis may not be able to take measurements due to the hearing prosthesis not correctly functioning or ceasing operations.

When these measurements are completed or when time allotted for taking measurements has elapsed, the switch mode voltage conversion circuit 310 is returned to it normal operation and the voltage returns to its normal state (e.g., 10 volts). It should be noted that the numbers in this example are arbitrary and selected to demonstrate the general concept of how the voltage may be boosted prior to commencement of the measurements.

FIG. 5 further illustrates the voltage 504 in a system that does not utilize boosting. As illustrated, the voltage more quickly approaches the lower limit (e.g., 5 volts) at which the cochlear implant system may operate. As such, the available time during which measurements may be taken is less than the amount of time available when the voltage is boosted as illustrated by voltage signal 502.

Measurement sequence controller 332 may further open switch 334 at block 412. This has the effect of turning off interfering circuits 364. This both reduces interference and prevents interfering circuits 364 from drawing power from power circuit 306 and prolongs the period of time that sensitive measurements may be taken (i.e., the amount of time before the voltage of power circuit 306 falls below the lower limit discussed above with reference to FIG. 5.) As noted above, these interfering circuits 364 may comprise communication circuits (both for internal and external communications) as well as non-essential high speed digital information processing circuits.

Shutting down or disabling non-essential internal or external communication circuits and non-essential high speed digital information processing circuits may reduce cross-coupled interference that may interfere with measurements taken by the hearing prosthesis. Because when shut down these circuits do not draw power, shutting down the circuits reduces internal power consumption of the system so as to conserve the available electrical energy capacitively stored by the switch mode voltage conversion circuit 310. This helps increase the amount of time that the switch mode voltage conversion circuit 310 may be shut off and measurements taken by the hearing prosthesis.

Measurement sequence controller 332 may adjust the operation of circuits 368 at block 414. Depending on the particular implementation, measurement sequence controller 332 may perform various functions in adjusting the performance of circuits 368. In one example, which will be discussed in more detail below, this may comprise adjusting the clock speeds of one or more of circuits 368.

As illustrated, each of blocks 404, 412, and 414 are performed in parallel. It should, however, be noted that this was provided for simplicity and in actual implementation that these steps may be performed sequentially or in different order.

After block 404-414 are performed, measurement sequence controller 332, at block 416, may direct sensitive measurement circuit 336 to commence with the sensitive measurements. Sensitive measurement circuit 336 may then use one or more of the circuits include in circuits 362, 366, and 368 in taking the sensitive measurements. In the example, of ECAP measurements, this may comprise directing one or more of the circuits included in circuits 362, 366, and 368 to apply a sub-threshold stimulation signal via one or more of electrode contacts 148 (FIG. 1) and then measuring the voltage detected via one or more of electrodes 148 (FIG. 1). ECAP measurements are well known to those skilled in the art, and the particulars of how ECAP measurements are obtained are not discussed further herein.

After the sensitive measurements are taken, measurement sequence controller 332 may direct the various components to return to normal operations at block 418. This may comprise sending instructions to switch mode voltage conversion circuit 310 to return to normal operations and their baseline output voltages. This may also comprise closing switch 334 and returning circuits 368 to their normal operating conditions.

Although in the above-discussed example, the voltage of power circuit 306 is not boosted prior to performance of the measurements, it should be noted that in other embodiments the voltage of power circuit 306 may be boosted prior to the measurements. For example, as noted above, energy storage 374 may comprise one or more capacitors. In an embodiment, measurement sequence controller 332 may direct the power circuit 306 to increase the power capacitively stored by such capacitors prior to performance of the measurements. This may be particularly useful, for example, in embodiments in which the energy storage component 374 does not comprise a battery and the power receiver 372 is shut off during performance of the measurements to reduce interference or the external component is directed to not transmit the power/data signal during performance of the measurements. Measurement sequence controller 332 may use various techniques depending on the particulars of the implementation for directing power circuit 306 to boost its voltage prior to commencement of the measurements. For example, measurement sequence controller 332 may direct the external component to boost the power provided via the power/data signal, or, for example, may direct circuitry in power circuit 306 to increase the power capacitively stored by power circuit 306.

Although FIG. 3 illustrates a power circuit 306 and a switch mode voltage conversion circuit 310, in other implementations, the stimulator unit 320 may have a plurality of power circuits and/or switch mode conversion circuits that each provide a different baseline voltage. In such embodiments, measurement sequence controller 322 may boost the voltage prior to measurement and/or shut down one or more or all of such circuits during the measurement using techniques such as those discussed above. Further, although the above description was discussed with reference to an embodiment in which the voltage of one type of power circuit (e.g., a switch mode voltage conversion circuit) is boosted prior to commencement of measurements, in other embodiments, the voltage of other types of power circuits that may or may not comprise a switch mode voltage conversion circuit may be boosted.

The sequencing, control, and processing of digital information within an implanted hearing prosthesis is usually initiated from high frequency fixed rate electrical signals derived from electrical and/or electro-mechanical resonator based, oscillator circuits. These oscillator-driven data sequencing or clocking circuits, together with the high frequency circuits they control, have the potential to couple sufficient interference into low-level measurement circuitry. As noted, in an embodiment, the hearing prosthesis may shut down or disable non-essential internal and/or external communications with high-speed digital information processing circuits to reduce cross-coupled interference at a time when measurements are to be undertaken.

Figure 6:
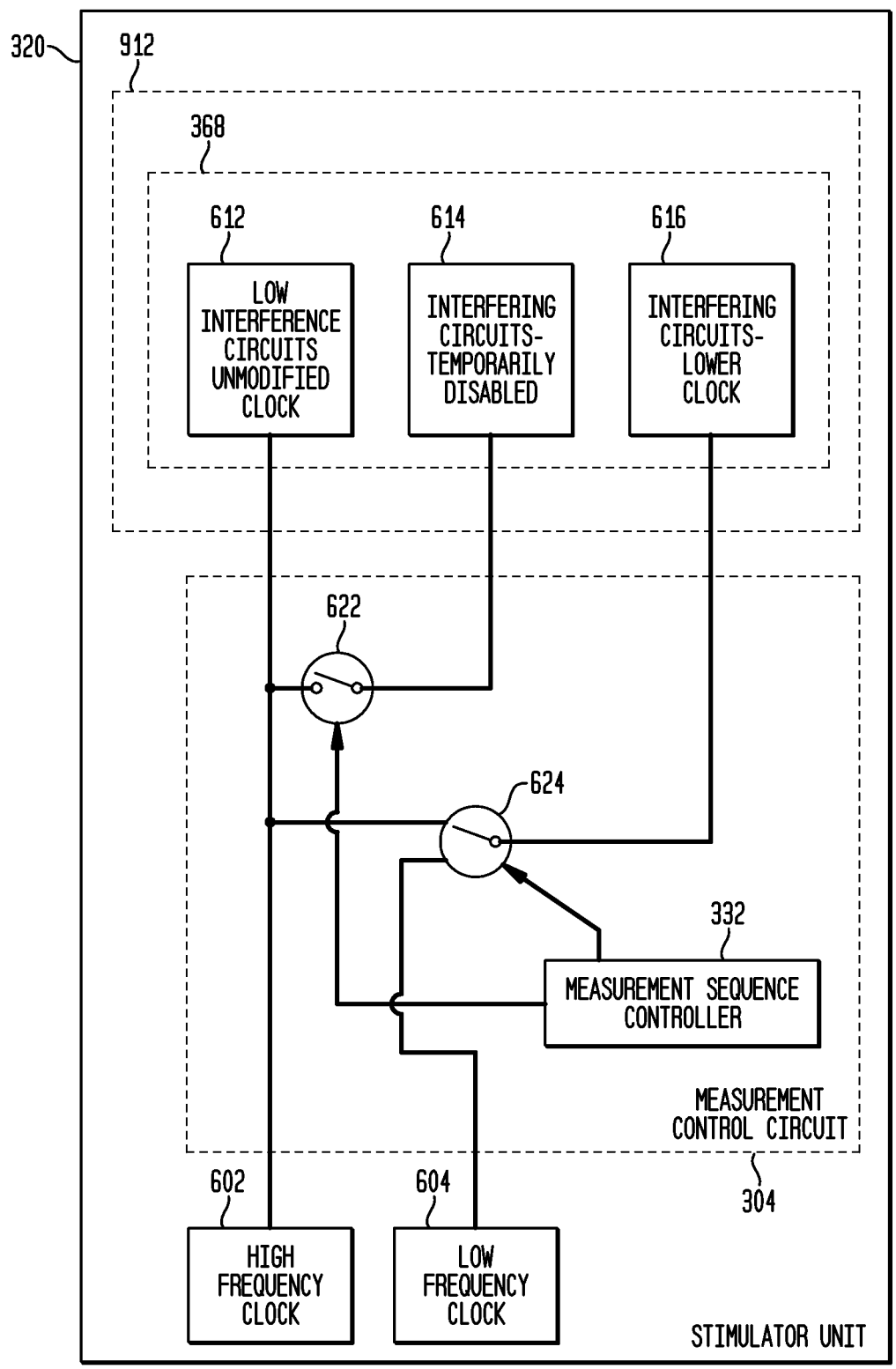
FIG. 6 is a simplified block diagram of exemplary circuitry for reducing interference, in accordance with an embodiment of the present invention.

As noted above, measurement sequence controller 332 may adjust the operation of circuits 336 to reduce interference at block 414. FIG. 6 is a simplified block diagram of exemplary circuitry included in stimulator unit 120 for explaining one illustrative example of how circuitry may be modified to reduce interference. In this example, the frequency of the clock signal provided to one or more of the circuits of circuits 362 is adjusted to reduce interference. For ease of explanation the majority of the circuits illustrated in FIG. 3 are omitted in FIG. 6.

As illustrated in FIG. 6, measurement control circuit 304 may comprise switches 622 and 624 that may be opened and closed to adjust the clock speed provided to particular circuits. These different clocks speeds may be provided by a high speed clock 602 and a low speed clock 604 included in stimulator unit 320.

As shown, circuits 368 may comprise low interference circuits 612 for which the clock speed is not adjusted, interfering circuits 614 that may be temporarily disabled by having their clock stopped, and interfering circuits 616 for which their clock speed may be reduced during sensitive measurements.

The low interference circuits 612 may include a real-time clock/main oscillator, a clock-shop, a measurement sequencer, a measurement ADC and buffering circuit included in stimulator unit 120. The interfering circuits 614 that may be temporarily disabled may include, for example, noisy circuitry tolerant of being temporarily disabled or shut down, signal processor(s), external communications circuit(s), and/or any other block not used during the measurement such as calibration, diagnostic, and controller circuits. The interfering circuits 616 that may have their clock speed reduced may include, for example, noisy circuitry able to function temporarily at lower clock rates, supervising microprocessor(s), and/or inter-module communications, handshaking, and/or watchdog circuits.

As illustrated, a switch 622 connects high frequency clock 602 and interfering circuits 614. During normal operations (e.g., when a measurement is not being undertaken), switch 622 is closed thereby providing interfering circuits 614 with a clock signal from high frequency clock 602. Also, as shown, a switch 624 is connected to both high frequency clock 602 and low frequency clock 604. Depending on which way switch 624 is connected either a high frequency clock signal from high frequency clock 602 or a low frequency clock signal from low frequency clock 604 is provided to interfering circuits 616. During normal operations (e.g., when a measurement is not being undertaken), switch 624 connects high frequency clock 602 to interfering circuits 616.

Figure 7:
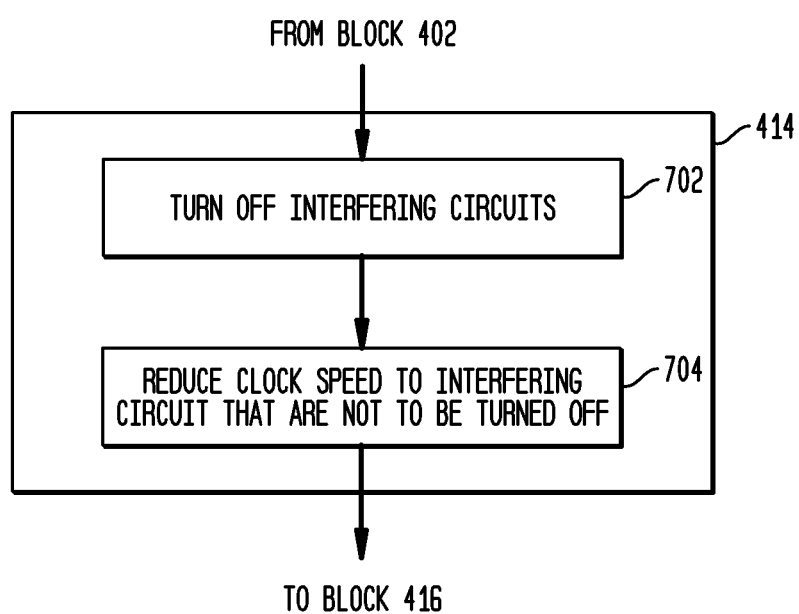
FIG. 7 is a flow chart of an exemplary method for adjusting the clock speeds of one or more circuits to reduce interference, in accordance with an embodiment of the present invention.

FIG. 7 is a flow chart of an exemplary method for adjusting the clock speeds of one or more circuits to reduce interference during sensitive measurements. FIG. 7 will be discussed with reference to stimulator unit 120 of FIG. 6 to help explain the operations of the components of measurement control circuit 304. The exemplary operations illustrated in FIG. 7 may be performed during block 414 of FIG. 4.

As illustrated, measurement sequence controller 332, at block 702, opens switch 622. This has the effect of turning off the clock to interfering circuits 614, and thus effectively shutting down circuits 614.

At block 704, measurement sequence controller 332 directs switch 624 to connect low frequency clock 604 to interfering circuits 616. This has the effect of reducing the frequency of the clock signal provided to interfering circuits 616 and thus helping reduce the amount of interference generated by interfering circuits 616. Additionally because the circuits may use less power when operating at a lower clock frequency, this may also help conserve the energy capacitively stored by switch mode voltage conversion circuit 310 and thus extend the period of time during which measurements may be taken.

After block 704, the sensitive measurements may be performed. After which, measurement sequence controller 332 returns switches 622 and 624 to their normal operating state.

Because the clock changes have the potential to disrupt or degrade the quality of the hearing benefit delivered to the recipient, in an embodiment, the sensitive measurement are performed during times when the hearing benefit will not be noticeably degraded. For example, the measurement sequence controller 332 may be configured to perform the measurements during specific time period(s) (e.g., at night when the recipient is expected to be sleeping). This may be especially beneficial for measurements that may require longer periods of time (e.g., greater than a few milliseconds). Further, in an embodiment, during the time period during which these measurements are taken, short duration sounds may be ignored by the stimulation unit 120 or temporarily stored in a buffer (e.g., a memory circuit) of the stimulator unit 120 and presented to the recipient a short period of time after the sensitive measurements are completed. This may be acceptable to a recipient during time periods (e.g., a night) when delaying low-level environmental sounds (e.g., up to a half second for an exemplary measurement) every half-hour (an exemplary time period between performance of measurements) may be acceptable or go undetected by the recipient.

It should be understood that the exemplary embodiment of FIGS. 6 and 7 is but one example of a mechanism that may be used to modify the behavior of one or more circuits to reduce interference during a measurement, and in other embodiments other mechanisms may be used. For example, in an embodiment, the clock speed of one or more clocks may be reduced during the measurement, 3 or more clock speeds may be used during the measurement, etc.

Figure 8:
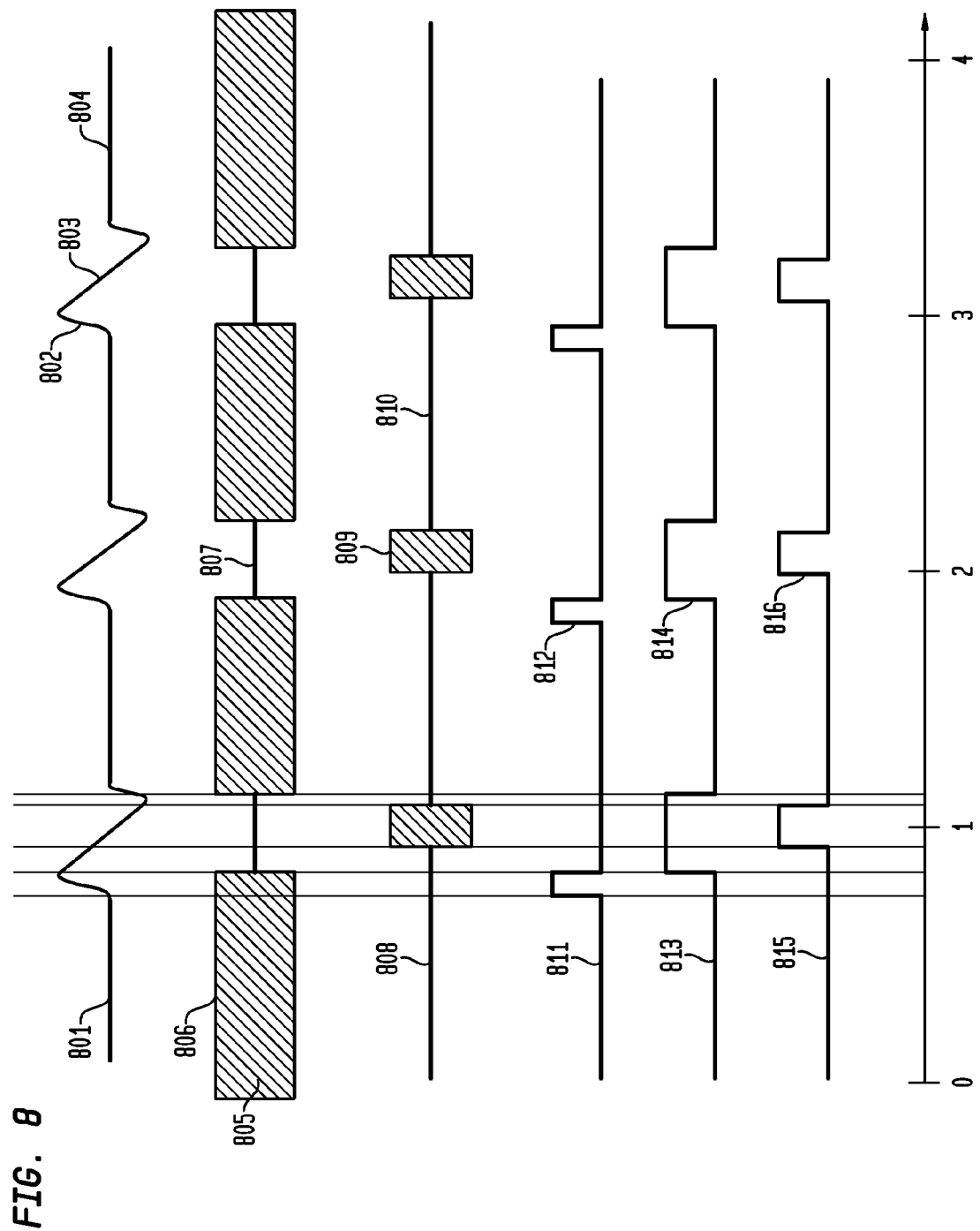
FIG. 8 illustrates an exemplary timing diagram, in accordance with an embodiment of the invention.

FIG. 8 illustrates an exemplary timing diagram, in accordance with an embodiment of the invention. This exemplary timing diagram may be, for example, the timing implemented in the exemplary stimulator unit of FIG. 3. Signal 801 illustrates an exemplary output of switch mode voltage conversion circuit 310. As illustrated, signal 801 is consistent with voltage signal 502 of FIG. 5. As shown, signal 801 is initially at its normal level 804 (i.e., the voltage level used during the application of stimulation to the recipient for generating a hearing percept. The voltage signal 801 is boosted during time period 802, and falls during time period 803, after which the signal 801 is returned to it normal level 804.

The next line 805 in FIG. 8 illustrates the time periods during which the hearing prosthesis is operating normally (illustrated by crosshatched rectangles 806) and applying stimulation to the recipient to generate a hearing percept, and time periods during which this operation is suspended or modified (illustrated by line 807 between rectangles 806).

The next line 808 in FIG. 8 illustrates the time periods during which sensitive measurements are undertaken (illustrated by crosshatched rectangles 809) and the time periods during which measurements are not taken (illustrated by line 810).

Line 811 illustrates a signal provided by measurement sequence controller 332 to switch mode voltage conversion circuit 310 directing the switch mode voltage conversion circuit 310 to either operate at its normal voltage or to increase its voltage. As illustrated, line 811 comprises pulses 812 that are used to direct the switch mode voltage conversion circuit 310 to boost its voltage. Then, when the pulse stops, the voltage is no longer increased and allowed to fall.

Line 813 illustrates a signal that may be used to shut down or modify interfering circuits. As illustrated, line 813 includes pulses 814. During the pulses 814, switches 334, 622, and 624 may switch to disable or modify respective circuit behavior as discussed above.

Line 815 illustrates a control signal that may be sent to sensitive measurement circuit 336 that includes pulses 816 that direct the sensitive measurement circuit 336 to perform the measurements.

It should be noted that FIG. 8 is but one example of an exemplary timing diagram representative of timings for performing the various operations discussed above with reference to FIGS. 3-7, and in other embodiments, other timings may be used.

Although the above exemplary embodiments were discussed with reference to a cochlear implant system, it should be noted that in other embodiments the hearing prosthesis may be other types of hearing prostheses, such as, for example, a bone conduction device, a direct acoustic cochlear stimulator (DACS), a middle ear mechanical stimulation device, or other types of bionic implant systems.

It is to be understood that the detailed description and specific examples, while indicating embodiments of the present invention, are given by way of illustration and not limitation. Many changes and modifications within the scope of the present invention may be made without departing from the spirit thereof, and the invention includes all such modifications.

What is claimed is:

1. A method for performing an evoked compound action potential (ECAP) measurement using a cochlear implant system having a switch mode voltage conversion circuit that interferes with the ECAP measurement while it is performed, the method comprising:
   supplying, with the switch mode voltage conversion circuit, voltage to an energy storage device;
   temporarily increasing the voltage supplied by the switch mode voltage conversion circuit to the energy storage device to boost an amount of energy stored in the energy storage device;
   after supplying increased voltage to the energy storage device for a period of time, shutting down the switch mode voltage conversion circuit; and
   while the switch mode voltage conversion circuit is shut down, performing the ECAP measurement using the energy stored in the energy storage device.

2. The method of claim 1, further comprising:
   restarting the switch mode voltage conversion circuit after performing the ECAP measurement.

3. The method of claim 1, wherein the energy storage device is a capacitor.

4. The method of claim 1, wherein the switch mode voltage conversion circuit is connected to the energy storage device via one or switches, and wherein shutting down the switch mode voltage conversion circuit comprises:
   opening at least one of the one or more switches that connect the switch mode voltage conversion circuit to the energy storage device.

5. The method of claim 1, further comprising:
   terminating power to a communications circuit configured to wirelessly communicate with an external device; and
   performing the ECAP measurement while the switch mode voltage conversion circuit is shut down and while power to the communication circuit is terminated.

6. The method of claim 5, further comprising:
   restoring power to the communications circuit after performing the ECAP measurement.

7. A method for performing an evoked compound action potential (ECAP) measurement using a cochlear implant system having a stimulator unit and having interfering circuits within the stimulator unit that interfere with the ECAP measurement while it is performed, the method comprising:
   terminating power to the interfering circuits; and
   performing the ECAP measurement using the cochlear implant system while the power to the interfering circuits is terminated.

8. The method of claim 7, further comprising:
   restoring power to the interfering circuits after the ECAP measurement is performed.

9. The method of claim 7, wherein the interfering circuits comprise one or more of communication circuits, signal processors, and microprocessors.

10. The method of claim 7, wherein terminating power to the interfering circuits comprises:
    opening at least one switch in the stimulator unit.

11. The method of claim 7, wherein terminating power to the interfering circuits comprises:
    turning off a clock within the stimulator unit to the interfering circuits.

12. The method of claim 7, further comprising
    reducing a frequency of a clock signal within the stimulator unit to the interfering circuits prior to performing the ECAP measurement;
    performing the ECAP measurement using the cochlear implant system while the frequency of the clock signal to the interfering circuits is reduced.

13. The method of claim 12, wherein reducing a frequency of a clock signal within the stimulator unit comprises:
    directing a switch within the stimulator unit to disconnect a high frequency clock from the interfering circuits and connect a low frequency clock to the interfering circuits.

14. The method of claim 12, further comprising:
    restoring the frequency of the clock signal after the ECAP measurement is performed.

15. A cochlear implant system comprising:
    a stimulation circuit configured to apply stimulation to recipient's cochlea to evoke a hearing percept;
    a power circuit configured to provide power to the stimulation circuit;
    a switch mode voltage conversion circuit connected to an energy storage device and configured to supply voltage to the energy storage device;
    a measurement control circuit configured to perform an evoked compound action potential (ECAP) measurement using the stimulation circuit; and
    a measurement sequence controller configured to, prior to performance of the ECAP measurement, instruct the switch mode voltage conversion circuit to temporarily increase the voltage supplied to the energy storage device, and to shut down the switch mode voltage conversion circuit during performance of the ECAP measurement.

16. The cochlear implant system of claim 15, wherein the energy storage device is a capacitor.

17. The cochlear implant system of claim 15, wherein, after performance of the ECAP measurement, the measurement sequence controller configured to restart the switch mode voltage conversion circuit.

18. The cochlear implant system of claim 15, wherein the switch mode voltage conversion circuit is connected to the energy storage device via one or switches, and wherein to shut down the switch mode voltage conversion circuit the measurement sequence controller is configured to open at least one of the one or more switches that connect the switch mode voltage conversion circuit to the energy storage device.

19. The cochlear implant system of claim 15, wherein the measurement sequence controller is further configured to terminate power to a communications circuit that wirelessly communicates with an external device and wherein the measurement control circuit is configured to perform the ECAP measurement while the switch mode voltage conversion circuit is shut down and while power to the communication circuit is terminated.

20. The cochlear implant system of claim 15, wherein the measurement sequence controller is further configured to restore power to the communications circuit after performance of the ECAP measurement.

\* \* \* \* \*